United States Patent
Endo et al.

(10) Patent No.: US 10,253,136 B2
(45) Date of Patent: Apr. 9, 2019

(54) COMPOUND AND EPOXY RESIN COMPOSITION CONTAINING SAME

(71) Applicant: ADEKA CORPORATION, Tokyo (JP)

(72) Inventors: Takeshi Endo, Fukuoka (JP); Kozo Matsumoto, Fukuoka (JP); Daisuke Sato, Saitama (JP); Ryo Ogawa, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 123 days.

(21) Appl. No.: 15/111,937

(22) PCT Filed: Jan. 22, 2015

(86) PCT No.: PCT/JP2015/051613
§ 371 (c)(1),
(2) Date: Jul. 15, 2016

(87) PCT Pub. No.: WO2015/118952
PCT Pub. Date: Aug. 13, 2015

(65) Prior Publication Data
US 2016/0333138 A1 Nov. 17, 2016

(30) Foreign Application Priority Data

Feb. 6, 2014 (JP) .................................. 2014-021055
Apr. 2, 2014 (JP) .................................. 2014-076349

(51) Int. Cl.
| C08G 59/50 | (2006.01) |
| C07D 233/58 | (2006.01) |
| C07D 239/06 | (2006.01) |
| C07D 249/08 | (2006.01) |
| C07D 251/14 | (2006.01) |
| C08L 63/00 | (2006.01) |
| C07D 235/06 | (2006.01) |
| C07D 235/08 | (2006.01) |

(52) U.S. Cl.
CPC ....... C08G 59/5073 (2013.01); C07D 233/58 (2013.01); C07D 235/06 (2013.01); C07D 235/08 (2013.01); C07D 239/06 (2013.01); C07D 249/08 (2013.01); C07D 251/14 (2013.01); C08L 63/00 (2013.01)

(58) Field of Classification Search
CPC .................................................. C08G 59/5073
See application file for complete search history.

(56) References Cited

U.S. PATENT DOCUMENTS

| 3,642,649 A | 2/1972 | Green et al. |
| 4,761,466 A | 8/1988 | Goel |
| 9,018,321 B2 | 4/2015 | Amano et al. |
| 2008/0209876 A1* | 9/2008 | Miller .............. G11C 13/0009 55/522 |
| 2009/0030158 A1 | 1/2009 | Amano et al. |
| 2010/0192814 A1* | 8/2010 | Herzog .................. C04B 26/02 108/161 |
| 2010/0256019 A1* | 10/2010 | Aston .................... C09K 8/035 507/128 |
| 2013/0214211 A1* | 8/2013 | Lehmann ................ C08K 5/17 252/506 |
| 2013/0305685 A1 | 11/2013 | Pelletier |
| 2014/0002226 A1 | 1/2014 | Moon et al. |
| 2015/0093310 A1* | 4/2015 | Bohringer ............... B01J 20/20 423/210 |

FOREIGN PATENT DOCUMENTS

| EP | 0458502 | 11/1991 |
| JP | 4-227924 | 8/1992 |
| JP | 2005-32551 | 2/2005 |
| JP | 2013-155105 | 8/2013 |
| JP | 2014-9357 | 1/2014 |

(Continued)

OTHER PUBLICATIONS

Hang Chen et al., "Electronic effect of ionic-pair substituents", Journal of Physical Organic Chemistry, 2013, vol. 26, No. 6, pp. 460-466.
Hossein Roohi et al., "Ion-pairs formed in [Mim+][N(CN)2-] ionic liquid: Structures, binding energies, NMR SSCCs, volumetric, thermodynamic and topological properties", Journal of Molecular Liquids, 2013, vol. 177, pp. 119-128.
International Search Report, PCT/JP2015/051613, dated Mar. 24, 2015.
Shaker, S.A. et al., Acta Crystallographica, Section E: Structure Reports Online, 2010, E66,o2913.
Yavorskii, N.P. et al., Farmatsevtichnii Zhurnal, 1973, vol. 28, No. 3, pp. 26-30.
Edwin, G. et al., Australian Journal of Chemistry, 1975, vol. 28, No. 4, pp. 909-912.
STN-Registry database, Chemical Abstracts Service, RN:1432017-50-9 and 1265472-59-0, Copyright 2017.

*Primary Examiner* — Megan McCulley
(74) *Attorney, Agent, or Firm* — Young & Thompson (57) ABSTRACT

An epoxy resin composition excellent in storage stability and curability is provided. Particularly, a compound of general formula (I) and an epoxy resin composition containing the compound as a curing agent are provided.

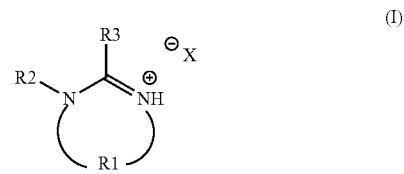

In formula (I), R1 is a hydrocarbon group optionally containing a nitrogen atom and capable of forming a cyclic structure optionally having a substituent; R2 is a hydrogen atom, an alkyl group, or an aryl group or is taken together with R1 to form an unsaturated bond; R3 is a hydrogen atom, an alkyl group, or an aryl group; and X is a dicyanamide ion or a thiocyanate ion.

3 Claims, 4 Drawing Sheets

(56) References Cited

FOREIGN PATENT DOCUMENTS

| JP | 2015-147742 | 8/2015 |
| WO | WO 2009014270 | 1/2009 |
| WO | WO 2012/042673 | 4/2012 |

\* cited by examiner

Fig. 1

$^1$H-NMR (400MHz, CD$_3$OD)

13C-NMR(100MHz, CD3OD)

COMPOUND AND EPOXY RESIN COMPOSITION CONTAINING SAME

TECHNICAL FIELD

This invention relates to a novel compound and an epoxy resin composition containing the same. More particular, it relates to a specific dicyanamide or thiocyanate salt and a one-pack type thermosetting epoxy resin composition containing the salt and having excellent storage stability and curability.

BACKGROUND ART

Epoxy resins exhibit high adhesion to various substrates. Cured products of epoxy resins have relatively excellent properties, such as heat resistance, chemical resistance, electric characteristics, and mechanical characteristics, and, are useful in a wide range of applications, including coatings, adhesives, and molding materials.

Conventional epoxy resin compositions are mostly of two-pack type in which an epoxy resin component is mixed with a curing agent or a curing accelerator on use. A two-pack type epoxy resin composition is characterized by curability at ambient or low temperature. Nevertheless, a two-pack epoxy resin composition is disadvantageous in that the two packs must be metered and mixed immediately before use and that the pot life of the composition is short and therefore has a limited use, for example, meeting difficulty in applying to automatic machinery. To eliminate these disadvantages, a one-pack type epoxy resin composition has been demanded.

In order to develop a one-pack type curing resin composition, a curing agent that does not react at room temperature but commences reaction to cure upon heating, i.e., a latent curing agent is necessary. Latent curing agents so far proposed include dicyandiamide, dibasic acid hydrazides, amine-boron trifluoride complex salts, guanamines, melamine, and imidazoles. They have, however, their own disadvantages. That is, mixtures of en epoxy resin with dicyandiamide, melamine, or guanamines are, while excellent in storage stability, problematic in that they need a high temperature (150° C. or higher) and a long time to cure. It is widely practiced to use a curing accelerator in combination to shorten the curing time, but this is accompanied by remarkable reduction in storage stability. On the other hand, compositions containing a dibasic acid dihydrazide or an imidazole cure at relatively low temperatures but have poor storage stability. While compositions containing an amine-boron trifluoride complex salt have high storage stability and cure in short times, they are poor in water resistance and corrosive to metals.

Patent Document 1 below proposes using an ionic liquid composed of, e.g., a combination of an ammonium- or phosphonium-based cation and a carboxylate anion as an epoxy resin curing agent. The results are still unsatisfactory.

CITATION LIST

Patent Document

Patent Document 1: US 2009/0030158

SUMMARY OF THE INVENTION

Problem to be Solved by the Invention

An object of the invention is to provide an epoxy resin composition excellent in storage stability and curability.

Means for Solving the Problem

As a result of extensive investigations with a view to accomplishing the above object, the inventors have found a specific dicyanamide or thiocyanate salt exhibits excellent effects as an epoxy resin curing agent and achieved the object of the invention. The invention has been completed based on this finding.

The invention provides a compound represented by general formula (I):

[Chem. 1]

(I)

wherein R1 represents a hydrocarbon group optionally containing a nitrogen atom and capable of forming a cyclic structure optionally having a substituent; R2 represents a hydrogen atom, an alkyl group, or an aryl group or is taken together with R1 to form an unsaturated bond; R3 represents a hydrogen atom, an alkyl group, or an aryl group; and X represents a dicyanamide ion or a thiocyanate ion.

The invention also provides an epoxy resin composition containing (A) epoxy resin and (B) a compound of general formula (I):

[Chem. 2]

(I)

wherein R1 represents a hydrocarbon group optionally containing a nitrogen atom and capable of forming a cyclic structure optionally having a substituent; R2 represents a hydrogen atom, an alkyl group, or an aryl group or is taken together with R1 to form an unsaturated bond; R3 represents a hydrogen atom, an alkyl group, or an aryl group; and X represents a dicyanamide ion or a thiocyanate ion.

Effect of the Invention

The invention provides a practically useful epoxy resin composition that is composed of easily available components and exhibits moderate curing characteristics and storage stability in good balance. In particular, the invention provides a one-pack type epoxy resin composition free from a curing resin component that is solid at ambient temperature, so that the resin composition has excellent workability and is suitable for application to tight, hard-to-reach places or impregnation application.

EMBODIMENTS FOR CARRYING OUT THE INVENTION

The invention will be described in detail with reference to its preferred embodiments. The novel compound represented by general formula (I) will first be described.

R1 in general formula (I) is a hydrocarbon group forming a cyclic structure together with the two nitrogen atoms with or without R2. The hydrocarbon group as R1 may contain a nitrogen atom and may contain an unsaturated bond. The number and the position of the nitrogen atom(s) and the number and the position of the unsaturated bond(s) are not limited.

Specific examples of the cyclic structure include 5-membered nitrogen-containing heterocyclic rings, such as imidazole, imidazoline, and triazole rings; 6-membered nitrogen-containing heterocyclic rings, such as pyrimidine and triazine rings; and nitrogen-containing heterocyclic rings formed by fusing the above heterocyclic rings to other rings, such as benzimidazole, benzotriazole, purine, pteridine, and quinazoline rings.

The cyclic structure may have a substituent. Examples of the substituent include alkyl groups having 1 to 10 carbon atoms, such as methyl, ethyl, propyl, isopropyl, butyl, isobutyl, t-butyl, amyl, isoamyl, t-amyl, hexyl, isohexyl, octyl, 2-ethylhexyl, t-octyl, nonyl, and decyl; aryl groups having 6 to 12 carbon atoms, such as phenyl and naphthyl; halogen atoms, such as fluorine, chlorine, bromine, and iodine; cyano, sulfo, hydroxyl, and nitro.

Examples of the alkyl group as represented by R2 and R3 include those having 1 to 10 carbon atoms, such as methyl, ethyl, propyl, isopropyl, butyl, isobutyl, t-butyl, amyl, isoamyl, t-amyl, hexyl, isohexyl, octyl, 2-ethylhexyl, t-octyl, nonyl, and decyl.

Examples of the aryl group as represented by R2 and R3 include those having 6 to 12 carbon atoms, such as phenyl and naphthyl.

Preferred examples of the compound of general formula (I) include compounds represented by formulae (I-1) through (I-5):

[Chem. 3]

(I-1)

-continued (I-2)

(I-3)

(I-4)

(I-5)

wherein R2', R3, R4, R5, R6, R7, R8, R9, R10, R11, R12, R13, R14, and R15 each independently represent a hydrogen atom, an alkyl group, or an aryl group; and X represents a dicyanamide ion or a thiocyanate ion.

Examples of the alkyl group as represented by R2', R3, R4, R5, R6, R7, R8, R9, R10, R11, R12, R13, R14, and R15 in general formulae (I-1) through (I-5) include those having 1 to 10 carbon atoms, such as methyl, ethyl, propyl, isopropyl, butyl, isobutyl, t-butyl, amyl, isoamyl, t-amyl, hexyl, isohexyl, octyl, 2-ethylhexyl, t-octyl, nonyl, and decyl. Examples of the aryl group as represented by R2', R3, R4, R5, R6, R7, R8, R9, R10, R11, R12, R13, R14, and R15 include those having 6 to 12 carbon atoms, such as phenyl and naphthyl.

Specific examples of the compound of general formula (I) in which X is a dicyanamide ion include, but are not limited to, compound Nos. 1-1 to 5-1 shown below.

[Chem. 4]

Compound No. 1-1 (Curing Agent A-1)

[Chem. 5]

Compound No. 2-1 (Curing Agent B-1)

[Chem. 6]

Compound No. 3-1 (Curing Agent B-1)

[Chem. 7]

Compound No. 4-1 (Curing Agent C-1)

[Chem. 8]

Compound No. 5-1

Specific examples of the compound of general formula (I) in which X is a thiocyanate ion include, but are not limited to, compound Nos. 1-2 to 5-2 shown below.

[Chem. 9]

Compound No. 1-2 (Curing Agent A-2)

[Chem. 10]

Compound No. 2-2 (Curing Agent B-2)

[Chem. 11]

Compound No. 3-2 (Curing Agent C-2)

[Chem. 12]

Compound No. 4-2

[Chem. 13]

Compound No. 5-2

While not being limited, the compound having general formula (I) in which X is a dicyanamide ion can be prepared by adding an acidic substance, such as hydrochloric acid, to a nitrogen-containing heterocyclic compound corresponding to a desired cation structure to form an intermediate (I-1), which is then caused to react with sodium dicyandiamide or a dicyandiamide salt in the presence of an alcohol or water as shown in the following reaction scheme:

[Chem. 14]

Intermediate (I-1)

The Compound of the invention wherein R1, R2, and R3 are the same groups as R1, R2 and R3 in the above-mentioned general formula (I).

While not being limited, the compound having general formula (I) in which X is a thiocyanate ion can be prepared by adding an acidic substance, such as hydrochloric acid, to a nitrogen-containing heterocyclic compound corresponding to a desired cation structure to form an intermediate (I-2), which is then caused to react with a thiocyanate, such as sodium thiocyanate, in the presence of an alcohol or water as shown in the following reaction scheme:

The compound having the formula (I) is obtainable from easily available starting materials and provides moderate curing characteristics and storage stability in good balance. Therefore, it is added to an epoxy resin as a thermosetting type latent curing agent to provide epoxy resin compositions for various applications described later.

The epoxy resin composition of the invention will next be described.

Examples of the epoxy resin that can be used in the epoxy resin composition of the invention as component (A) include polyglycidyl ethers of mononuclear polyhydric phenol compounds, such as hydroquinone, resorcin, pyrocatechol, and phloroglucinol; polyglycidyl ethers of polynuclear polyhydric phenol compounds, such as dihydroxynaphthalene, biphenol, methylenebisphenol (i.e., bisphenol F), methylenebis(ortho-cresol), ethylidenebisphenol, isopropylidenebisphenol (i.e., bisphenol A), isopropylidenebis(ortho-cresol), tetrabromobisphenol A, 1,3-bis(4-hydroxycumylbenzene), 1,4-bis(4-hydroxycumylbenzene), 1,1,3-tris(4-hydroxyphenyl)butane, 1,1,2,2-tetra(4-hydroxyphenyl)ethane, thiobisphenol, sulfobisphenol, oxybisphenol, phenol novolak, ortho-cresol novolak, ethylphenol novolak, butylphenol novolak, octylphenol novolak, resorcin novolak, and terpenediphenol; polyglycidyl ethers of polyhydric alcohols, such as ethylene glycol, propylene, glycol, butylene glycol, hexanediol, polyglycol, thiodiglycol, glycerol, trimethylolpropane, pentaerythritol, sorbitol, and bisphenol A ethylene oxide adducts; homo- or copolymers of glycidyl esters of aliphatic, aromatic or alicyclic polybasic acids, such as maleic acid, fumaric acid, itaconic acid, succinic acid, glutaric acid, suberic acid, adipic acid, azelaic acid, sebacic acid, dimer acid, trimer acid, phthalic acid, isophthalic acid, terephthalic acid, trimellitic acid, trimesic acid, pyromellitic acid, tetrahydrophthalic acid, hexahydrophthalic acid, and endomethylenetetrahydrophthalic acid, and glycidyl methacrylate; epoxy compounds having a glycidylamino group, such as N,N-diglycidylaniline, bis(4-(N-methyl-N-glycidylamino)phenyl)methane, and diglycidyl o-toluidine; epoxidized cyclic olefin compounds, such as vinylcyclohexene diepoxide, dicyclopentanediene diepoxide, 3,4-epoxycyclohexylmethyl 3,4-epoxycyclohexanecarboxylate, 3,4-epoxy-6-methylcyclohexylmethyl 6-methylcyclohexanecarboxylate, and bis(3,4-epoxy-6-methylcyclohexylmethyl) adipate; epoxidized conjugated diene polymers, such as epoxidized polybutadiene and epoxidized styrene-butadiene copolymers; and heterocyclic compounds, such as triglycidyl isocyanurate. These polyepoxy compounds may be internally crosslinked by an isocyanate-terminated prepolymer or may have their molecular weight increased using a polyfunctional polyhydric active hydrogen compound, e.g., a polyhydric phenol, a polyamine, a carbonyl-containing compound, or a polyphosphoric ester.

Preferred of the recited epoxy resins (A) are polyglycidyl ethers of polynuclear polyhydric phenol compounds in terms of workability and curability, with bisphenol F and bisphenol A being more preferred.

The epoxy resin (A) preferably has an epoxy equivalent of from 70 to 3,000, more preferably 90 to 2,000. With an epoxy equivalent less than 70, the physical properties of the cured product can reduce. With an epoxy equivalent larger than 3,000, curability can be insufficient.

Component (B) that can be used in the epoxy resin composition of the invention is the compound of general formula (I), the examples of which have been described. Preferred examples of the compound (B) of formula (I) include those of formulae (I-1) to (I-5).

The amount of the compound (B) of formula (I) used in the epoxy resin composition of the invention is preferably 0.1 to 50 parts, more preferably 1 to 20 parts, by mass per 100 parts by mass of the epoxy resin (A). If the content of compound (B) is less than 0.1 parts, insufficient cure can result. If it exceeds 50 parts, the storage stability of the epoxy resin composition can be impaired considerably.

If necessary, the epoxy resin composition may contain commonly used additives, including other curing agents except the compound (B) of formula (I); curing catalysts; reactive or nonreactive diluents (plasticizers), such as monoglycidyl ethers, dioctyl phthalate, dibutyl phthalate, benzyl alcohol, and coal tar; fillers or pigments, such as glass fiber, carbon fiber, cellulose, silica sand, cement, kaolin, clay, aluminum hydroxide, bentonite, talc, silica, finely divided silica, titanium dioxide, carbon black, graphite, iron oxide, and bituminous materials; silane coupling agents, such as γ-aminopropyltriethoxysilane, N-β-(aminoethyl)-γ-aminopropyltriethoxysilane, N-β-(aminoethyl)-N-β-(aminoethyl)-γ-aminopropyltriethoxysilane, γ-anilinopropyltriethoxysilane, γ-glycidoxypropyltriethoxysilane, γ-(3,4-epoxycyclohexyl)ethyltriethoxysilane, vinyl triethoxysilane, N-γ-(N-vinylbenzylaminoethyl)-γ-aminopropyltriethoxysilane, γ-methacryloxypropyltrimethoxysilane, γ-chloropropyltrimethoxy silane, and γ-mercaptopropyltrimethoxysilane; lubricants, such as candelilla wax, carnauba wax, Japan wax, insect wax, beeswax, lanolin, spermaceti wax, montan wax, petroleum wax, fatty acid waxes, fatty acid esters, fatty acid ethers, aromatic esters, and aromatic ethers; thickeners; thixotropic agents; antioxidants; light stabilizers; UV absorbers; flame retardants; defoamers; rust inhibitors; colloidal silica, and colloidal alumina. Adhesive resins, such as xylene resin and petroleum resins, may be used in combination.

The epoxy resin composition of the invention can be used for a wide range of applications, such as coatings or adhesives for concrete, cement mortar, various metals, leather, glass, rubber, plastics, wood, cloth, and paper; pressure-sensitive adhesives for packaging adhesive tape, adhesive labels, labels for frozen foods, removable labels, labels for POS system, adhesive wallpaper, and adhesive flooring; processed paper, such as art paper, light-weight coated paper, cast-coated paper, coated paperboard, carbonless copy paper, and impregnated paper; textile processing agents, such as sizing agents, anti-fray agents, and processing agents for natural fibers, synthetic fibers, glass fiber, carbon fiber, and metal fibers; building materials, such as sealants, cement admixtures, and waterproof materials; and sealants for electronic/electric devices.

EXAMPLES

The invention will now be illustrated in greater detail with reference to Preparation Examples and Examples, but it should be understood that the invention is not deemed to be limited thereto.

Preparation Example 1-1 (Preparation of Intermediate A-1)

In 40 ml of water was dissolved. 1.8 g (20 mmol) of sodium dicyanamide. While stirring at 25° C., 200 g (20 mmol) of a 0.1 M silver nitrate aqueous solution was added thereto dropwise to cause reaction for 2 hours. The precipitate formed was collected by filtration and dried to give 3.3 g of intermediate A-1 ($Ag^+N(CN)_2^-$) as pale yellow powder.

Preparation Example 1-2 (Preparation of Intermediate A-2)

In 40 ml of water was dissolved 1.6 g (20 mmol) of sodium thiocyanate. While stirring at 25° C., 200 g (20 mmol) of a 0.1 M silver nitrate aqueous solution was added thereto dropwise to cause reaction for 2 hours. The precipitate formed was collected by filtration and dried to give 2.3 g of intermediate A-2 ($Ag^+(SCN)^-$) as pale yellow powder.

Preparation Example 2 (Preparation of Intermediate B)

In 55 ml of methanol was dissolved 4.5 g (55 mmol) of 1-methylimidazole. While stirring at 25° C., 5.8 g (55 mmol) of a 35% hydrochloric acid aqueous solution was added thereto dropwise to cause reaction for 1 hour. The solvent was removed on an evaporator, and the residue was dried under reduced pressure to give 6.6 g of intermediate B (a compound represented by the formula below) as pale brown solid.

[Chem. 16]

Intermediate B

Preparation Example 3 (Preparation of Intermediate C)

In 43 ml of methanol was dissolved 4.7 g (43 mmol) of 2-ethyl-4-methylimidazole. While stirring at 25° C., 4.5 g (43 mmol) of a 35% hydrochloric acid aqueous solution was added thereto dropwise to cause reaction for 1 hour. The solvent was removed on an evaporator, and the residue was dried under reduced pressure to give 5.9 g of intermediate C (a compound represented by the formula below) as pale yellow powder.

[Chem. 17]

Intermediate C

Preparation Example 4 (Preparation of Intermediate D

In 26 ml of methanol was dissolved 2.6 g (26 mmol) of 1-methyl-1,4,5,6-tetrahydropyrimidine. While stirring at 25° C., 2.7 g (26 mmol) of a 35% hydrochloric acid aqueous solution was added thereto dropwise to cause reaction for 1 hour. The solvent was removed on an evaporator, and the residue was dried under reduced pressure to give 3.7 g of intermediate D (a compound represented by the formula below) as pale yellow powder.

[Chem. 18]

Intermediate D

Example 1-1 (Preparation of Curing Agent A-1)

In 17 ml of water was dissolved 1.0 g (8.5 mmol) of intermediate B. While stirring at 25° C., 1.5 g (8.5 mmol) of intermediate A-1 was added thereto in divided portions to cause reaction for 24 hours. The solvent was removed on an evaporator, and the residue was dried under reduced pressure to furnish 1.2 g of curing agent A-1 as pale yellow liquid.

Example 1-2 (Preparation of Curing Agent A-2)

In 17 ml of water was dissolved 1.0 g (8.5 mmol) of intermediate B. While stirring at 25° C., 1.0 g (8.5 mmol) of intermediate A-2 was added thereto in divided portions to cause reaction for 24 hours. The solvent was removed on an evaporator, and the residue was dried under reduced pressure to furnish 1.1 g of curing agent A-2 as pale yellow liquid.

Example 2-1 (Preparation of Curing Agent B-1)

Figure 1:
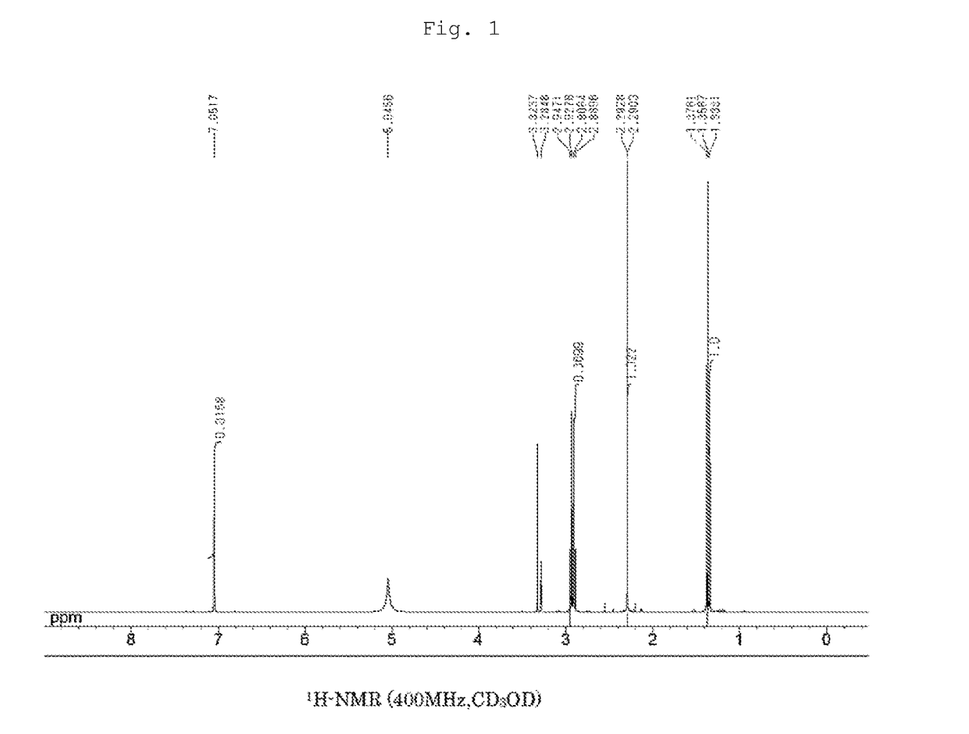
FIG. 1 is a $^1$H-NMR spectrum of curing agent B-1 (compound No. 2-1) prepared in Example 2-1.
Figure 2:
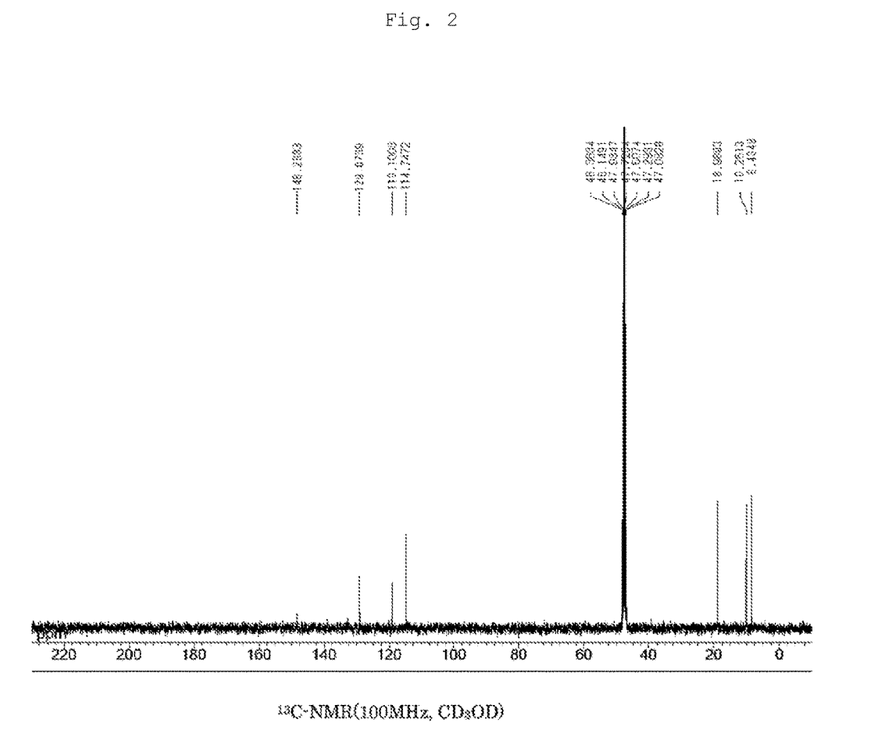
FIG. 2 is a $^{13}$C-NMR spectrum of curing agent B-1 (compound No. 2-1) prepared in Example 2-1.

In 20 ml of water was dissolved 1.5 g (10.0 mmol) of intermediate C. While stirring at 25° C., 1.7 g (10.0 mmol) of intermediate A-1 was added thereto in divided portions to cause reaction for 24 hours. The solvent was removed on an evaporator, and the residue was dried under reduced pressure to furnish 1.7 g of curing agent B as pale yellow powder. The resulting curing agent B-1 was identified by $^1$H-NMR and $^{13}$C-NMR. The resulting $^1$H-NMR and $^{13}$C-NMR spectra are shown in FIGS. 1 and 2, respectively.
Results of Identification:
$^1$H-NMR (400 MHz, CD$_3$OD) d: 1.36 (3H, t, J=7.6 Hz), 2.29 (3H, d, J=1.0 Hz), 2.92 (2H, q, J=7.7 Hz), 7.05 (1H, s)
$^{13}$C-NMR (100 MHz, CD$_3$OD) d: 8.4, 10.3, 19.0, 114.7, 119.1, 129.1, 148.3

Example 2-2 (Preparation of Curing Agent B-2)

Figure 3:
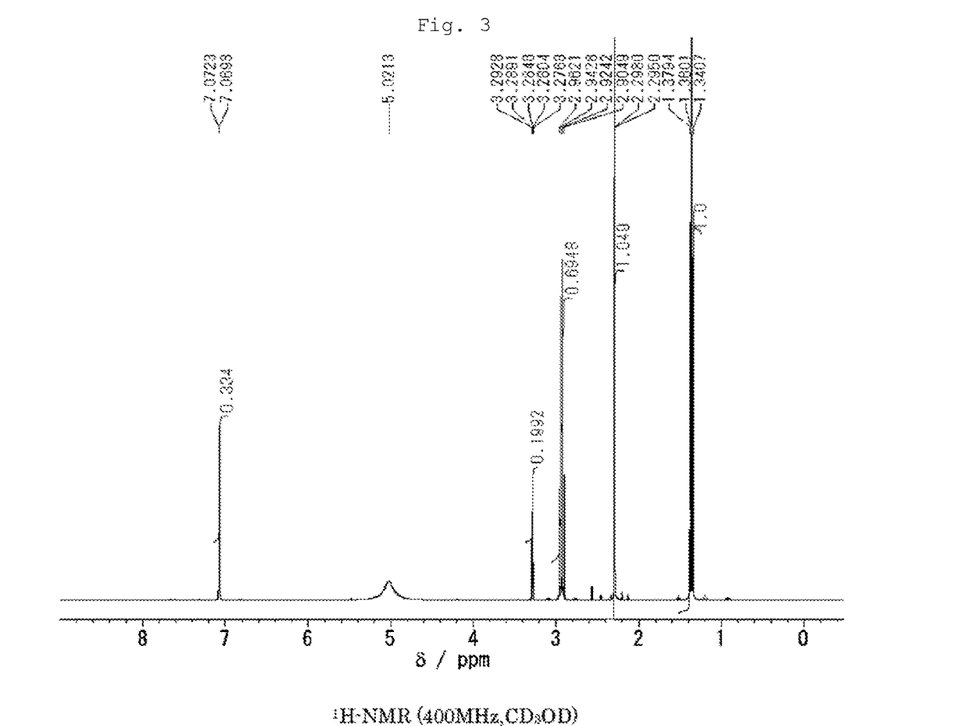
FIG. 3 is a $^1$H-NMR spectrum of curing agent B-2 (Compound No. 2-2) prepared in Example 2-2.
Figure 4:
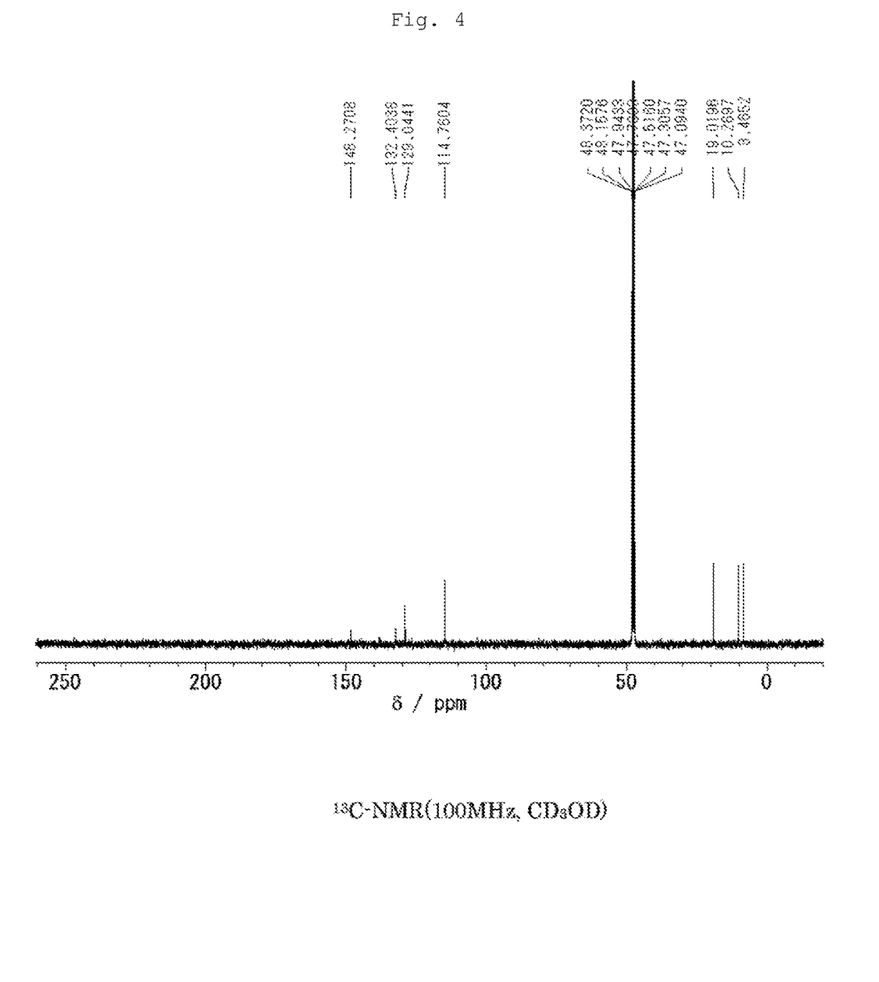
FIG. 4 is a $^{13}$C-NMR spectrum of curing agent B-2 (compound NO. 2-2) prepared in Example 2-2.

In 20 ml of water was dissolved 1.5 g (10.0 mmol) of intermediate C. While stirring at 25° C., 1.2 g (10.0 mmol) of intermediate A-2 was added thereto in divided portions to cause reaction for 24 hours. The solvent was removed on an evaporator, and the residue was dried under reduced pressure to furnish 1.6 g of curing agent B-2 as pale yellow powder. The resulting curing agent B-2 was identified by $^1$H-NMR and $^{13}$C-NMR. The resulting $^1$H-NMR and $^{13}$C-NMR spectra are shown in FIGS. 3 and 4, respectively.
Results of Identification:
$^1$H-NMR (400 MHz, CD$_3$OD) d: 1.36 (3H, t, J=7.8 Hz), 2.30 (3H, d, J=1.2 Hz), 2.93 (2H, q, J=7.6 Hz), 7.07 (1H, d, J=1.2 Hz)
$^{13}$C-NMR (100 MHz, CD$_3$OD) d: 8.5, 10.3, 19.0, 114.8, 129.0, 132.4, 148.3

Example 3-1 (Preparation of Curing Agent C-1)

In 40 ml of water was dissolved 1.2 g (9.2 mmol) of intermediate D. While stirring at 25° C., 1.6 g (9.2 mmol) of intermediate A-1 was added thereto in divided portions to cause reaction for 24 hours. The solvent was removed on an evaporator, and the residue was dried under reduced pressure to afford 1.4 g of curing agent C-1 as pale yellow liquid.

Example 3-2 (Preparation of Curing Agent C-2)

In 40 ml of water was dissolved 1.2 g (9.2 mmol) of intermediate D. While stirring at 25° C., 1.1 g (9.2 mmol) of intermediate A-2 was added thereto in divided portions to cause reaction for 24 hours. The solvent was removed on an evaporator, and the residue was dried under reduced pressure to give 1.3 g of curing agent C-2 as pale yellow liquid.

Example 4-1 (Preparation of One-pack Type Epoxy Resin Composition A-1)

One-pack type epoxy resin composition A-1 was prepared by uniformly mixing 340 g of Adeka Resin EP-4100L from Adeka Corp. (bisphenol A diglycidyl ether epoxy resin; epoxy equivalent: 170 g/eq.; total chlorine content: 600 ppm) with 15 g of curing agent A-1, followed by thoroughly defoaming under reduced pressure at room temperature.

Example 4-2 (Preparation of One-pack Type Epoxy Resin Composition A-2)

One-pack type epoxy resin composition A-2 was prepared by uniformly mixing 340 g of Adeka Resin EP-4100L from Adeka Corp. (bisphenol A diglycidyl ether epoxy resin; epoxy equivalent: 170 g/eq.; total chlorine content: 600 ppm) with 14.1 g of curing agent A-2, followed by thoroughly defoaming under reduced pressure at room temperature.

Example 5-1 (Preparation of One-pack Type Epoxy Resin Composition B-1)

One-pack type epoxy resin composition B-1 was prepared in the same manner as in Example 4, except for using 17.7 g of curing agent B-1.

Example 5-2 (Preparation of One-pack Type Epoxy Resin Composition B-2)

One-pack type epoxy resin composition B-2 was prepared in the same manner as in Example 4-2, except for using 16.9 g of curing agent B-2.

Example 6-1 (Preparation of One-pack Type Epoxy Resin Composition C-1)

One-pack type epoxy resin composition C-1 was prepared in the same manner as in Example 4-1, except for using 16.5 g of curing agent C-1.

Example 6-2 (Preparation of One-pack Type Epoxy Resin Composition C-2)

One-pack type epoxy resin composition C-2 was prepared in the same manner as in Example 4-2, except for using 15.7 g of curing agent C-2.

Comparative Example 1 (Preparation of One-pack Type Epoxy Resin Composition D)

One-pack type epoxy resin composition D was prepared in the same manner as in Example 4-1, except for using 8.2 g of 1-methylimidazole.

Comparative Example 2 (Preparation of One-pack Type Epoxy Resin Composition E)

One-pack type epoxy resin composition E was prepared in the same manner as in Example 4-1, except for using 11 g of 2-ethyl-4-methylimidazole.

Comparative Example 3 (Preparation of One-pack Type Epoxy Resin Composition F)

One-pack type epoxy resin composition D was prepared in the same manner as in Example 4-1, except for using 9.8 g of 1-methyl-1,4,5,6-tetrahydropyrimidine.

The one-pack type epoxy resin compositions obtained in Examples and Comparative Examples were evaluated for physical properties in accordance with the following methods.
Method of Evaluation:
(1) One-Pack Stability Test
The one-pack type epoxy resin composition was stored hermetically at 40° C. immediately after the preparation. The time required for the composition to lose flowability was recorded as a measure for evaluating one-pack stability.
(2) Curability
The one-pack type epoxy resin composition was caused to gel on a hot plate at 150° C. and 180° C. The gelling time was recorded to evaluate curability.

Results of Evaluation:

TABLE 1

|  | | Example 4-1 | Comp. Example 1 | Example 5-1 | Comp. Example 2 | Example 6-1 | Comp. Example 3 |
|---|---|---|---|---|---|---|---|
| One-pack Stability (hr) | | 48 | 12 | 48 | 6 | >200 | 72 |
| Gel Time (min) | 150° C. | 1'45" | 1'55" | 1'10" | 1'12" | >60 | >60 |
|  | 180° C. | 0'45" | 0'48" | 0'30" | 0'30" | 35 | >60 |

TABLE 2

|  | | Example 4-2 | Comp. Example 1 | Example 5-2 | Comp. Example 2 | Example 6-2 | Comp. Example 3 |
|---|---|---|---|---|---|---|---|
| One-pack Stability (hr) | | 48 | 12 | 48 | 6 | >200 | 72 |
| Gel Time (hr) | 150° C. | 1'50" | 1'55" | 1'05" | 2'07" | >60 | >60 |
|  | 180° C. | 0'20" | 0'48" | 0'30" | 1'02" | 28 | >60 |

As is apparent from the results in Tables 1 and 2, the use of the nitrogen-containing salt compound having a dicyanamide or thiocyanate anion structure as a thermosetting type latent curing agent for epoxy resins provides a one-pack type epoxy resin composition excellent in not only one-pack stability but curability.

The invention claimed is:

1. A compound represented by a general formula of:

(I-2)

wherein R2', R3, R6, R7, and R8 each independently represent a hydrogen atom, an alkyl group, or an aryl group; and X represents a dicyanamide ion.

2. An epoxy resin composition comprising (A) an epoxy resin and (B) a compound represented by general formula selected from the group consisting of:

(I-2)

(I-3)

and (I-4)

and wherein R2', R3, R6, R7, R8, R9, R10, and R11, each independently represent a hydrogen atom, an alkyl group, or an aryl group; and X represents a dicyanamide ion.

3. The epoxy resin composition of claim 2, being a one-pack thermosetting epoxy resin composition.

* * * * *